April 14, 1970 J. D. GIESY Re. 26,854

APPARATUS FOR OBTAINING URINE SAMPLES

Original Filed Aug. 28, 1964

Jerry D. Giesy
INVENTOR.

BY Ramsey, Kolisch & Hartwell
Attys.

United States Patent Office

Re. 26,854
Reissued Apr. 14, 1970

26,854

APPARATUS FOR OBTAINING URINE SAMPLES

Jerry D. Giesy, 8335 SW. Ridgeway Drive,
Portland, Oreg. 97225

Original No. 3,335,714, dated Aug. 15, 1967, Ser. No. 392,745, Aug. 28, 1964. Application for reissue July 15, 1969, Ser. No. 848,370
Int. Cl. A61b *5/00;* A61f *5/44;* A61g *9/00*
U.S. Cl. 128—2 5 Claims

Matter enclosed in heavy brackets [ ] appears in the original patent but forms no part of this reissue specification; matter printed in italics indicates the additions made by reissue.

*ABSTRACT OF THE DISCLOSURE*

*An apparatus for collecting uncontaminated wine samples from female patients includes a container with an elongated tube sealingly mounted in the open end of the container. The tube on its distal end includes a compressible and resilient pad portion which is adapted to be poistioned to produce close encirclement of the urethral meatus to form a seal thereabout and provide urine samples free from extraurethral contamination.*

This invention relates to collecting urine samples from female patients, where special problems are introduced in obtaining urine samples free from extraurethral contamination.

Medical science has become increasingly aware of the importance of obtaining urine samples in performing a thorough examination of a patient. It has been discovered, for instance, that in the vast majority of cases, urine samples collected from patients either show very few bacteria, or a bacteria count which is many times what is usual. A low bacteria count is indicative of a normal condition, while a high bacteria count often indicates an unhealthy condition which suitable diagnosis may correct. A bacteria count falling between these low and high ranges is a relatively rare event. Thus, in order that urine analysis be a useful diagnostic tool for the physician, it is important that a means be devised that makes possible the taking of urine samples where the bacteria therein is an accurate reflection of the condition of the urine as it exists in the bladder.

In the female, because of the position of the urethra, difficulties have been encountered in obtaining truly representative urine samples. Commonly, such samples are obtained by inserting a catheter into the urethra, with urine then flowing directly from the bladder. This, however, has the potential danger of introducing bacteria into what previously was a sterile bladder, a particularly disadvantageous feature with patients susceptible to urinary tract infections. With other techniques, urine samples frequently are contaminated with bacteria derived from extraurethral sources, such as the vagina, so that the samples do not show the condition of the urine as it exists in the bladder.

Generally, an object of the invention is to provide a device for obtaining urine samples from the urethra, where such samples are collected without penetration of the urethra and are relatively free of extraurethral contamination.

More specifically, an object is to produce such a device which includes means that forms a relatively tight seal about the meatus of the urethra, such seal defining a zone which excludes regions outside the urethra from where extraurethral contamination might be derived.

Yet a further object is to provide a device for taking urine samples which may be placed simply and rapidly in operative, urine-collecting position. The device features means which senses the anterior vaginal wall and with reference to this wall properly positions the sealing means described. The device is particularly well adapted to be used with the patient in a sitting position.

Yet another object is to provide a novel method for obtaining urine samples from females, which relies upon establishing a sealed zone about the meatus of the urethra, with such zone being properly positioned by reference to the anterior vaginal wall but excluding the vagina proper and adjoining areas.

These and other objects and advantages are obtained by the invention, and the same is described in connection with the accompanying drawings, wherein.

Figure 2:
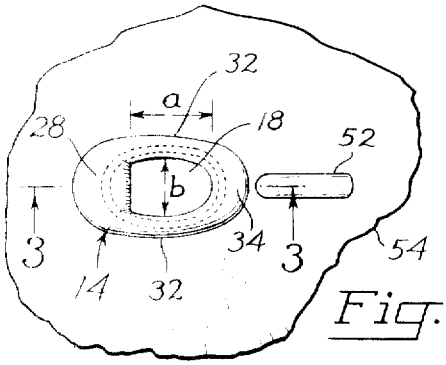
FIG. 2 is a top view of the apparatus in FIG. 1.

Referring now to the drawings, it will be noted that the apparatus illustrated comprises an elongated tubular body 10, comprising tube 12, and mounted on an end 12a of this tube, an annular pad indicated at 14.

Tube 12 preferably is made of a rigid or semirigid material, such as "Pyrex," to enable suitable positioning of end 12a thereof by manipulation of ends 12b. Pad 14 may be of compressible and resilient relatively soft material, whereby a cushion is formed at one end of the tubular body, and by way of example may be made of foamed rubber or other elastomer.

Extending along through the tube is a channel 16. Pad 14 has a center opening extending therethrough, shown at 18, and opening 18 and channel 16 together form a passage extending the length of the tubular body with an entrance end adjacent end 12a of tube 12.

It will be noted that tube 12 is bent at 20 between the ends thereof, so that tubular body 10 has a concavo-convex outline viewing a side profile thereof. Thus, two reaches of tube are present which extend out to opposite ends of the tube and which define an obtuse angle, shown at A. This angle in a typical case may be in the range of 165°, plus or minus 5°.

Figure 1:
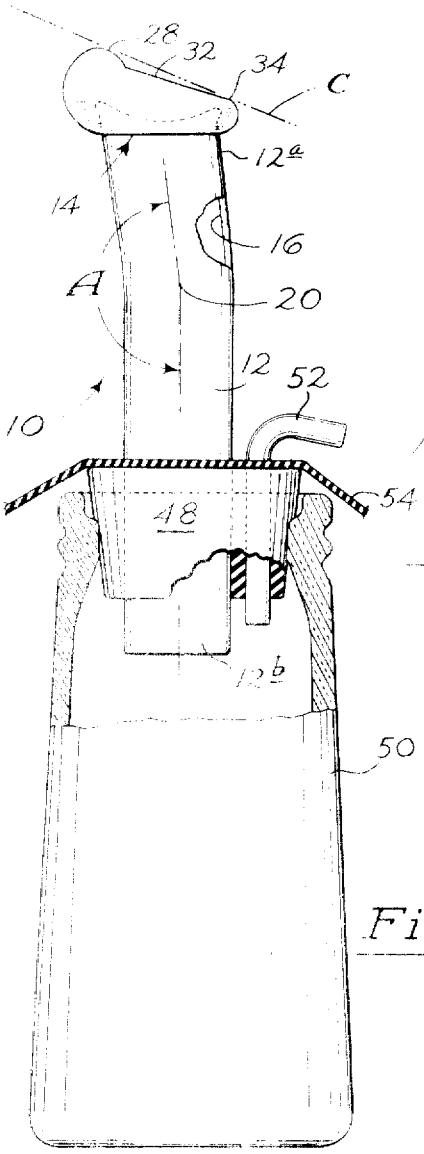
FIG. 1 illustrates apparatus as contemplated herein, with portions broken away, such including a tubular body and a container for collecting urine mounted on one end of the tubular body.

The upper end of the tubular body in FIG. 1, i.e., end 12a of the tube and pad 14, is placed between the labia of a female when taking a urine sample, and to facilitate such positioning, end 12a of tube 12 may be flattened slightly, as best shown in FIG. 2, whereby a somewhat elliptical outline is given to the cross section thereof. This outline is shared by cushion or pad 14.

At end 12a of tube 12, opposite lateral sides of the tube are shown bounded by concave edges such as the one indicated at 24. Pad 14 is grooved at 26 on the underside thereof and this groove receives the edges bounding the end of the tube including edges 24.

Figure 3:
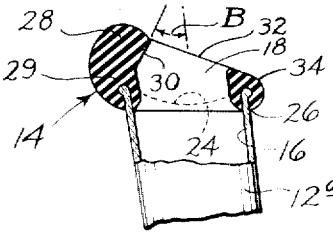
FIG. 3 is a cross sectional view, taken along the line 3—3 in FIG. 2.

As best shown in FIGS. 2 and 3, pad 14 includes a shoulder 28 located beyond end 12a of the tube and supported by a wall 29 adjacent one side of tube 12. A surface 30 bounds shoulder 28 on the inside of the shoulder, and, as best illustrated in FIG. 3 by the angle B, the surface slopes away from the axis of passage 12 progressing axially inwardly from the end of the tubular body. Integral with opposite ends of shoulder 28 are lip portions 32, and these smoothly meet with a heel portion 34, the heel and lip portions also being beyond end 12a of the tube. Wall 29 is flexible, and thus permits shoulder 28 to flex outwardly (or to the left in FIG. 3) when the device is used. Lip portions 32 joining with the shoulder are stretchable and elongate when shoulder 28 is bent outwardly. With the pad of compressible, resilient material, they are also compressible to a degree, in an axially inward direction at the end of the tubular body.

As best shown in FIG. 1, the outer end of shoulder 28, the lip portions, and the outer part of portion 34 generally define a plane C which is inclined from perpendicularity to the axis of the tube adjacent end 12a. Describing the relationship in another way, the heel portion is disposed inwardly toward end 12a of the tube from a plane passing through the outermost extremity of the shoulder and normal to the axis of end 12a of the tube.

Further describing the device, lower end 12b of the tube extends through a stopper 48 which is employed to mount the tube in the top of a flask or container 50, with the passage within tube 12 communicating with the interior of the flask. At 52 is indicated a vent conduit which communicates with the interior of the flask through the stopper. A diaphragm 54 forms a dam between the top of the flask and upper portions of tube 20. Thus, the crevice around the stopper where the stopper meets the neck of the flask is covered.

Figure 4:
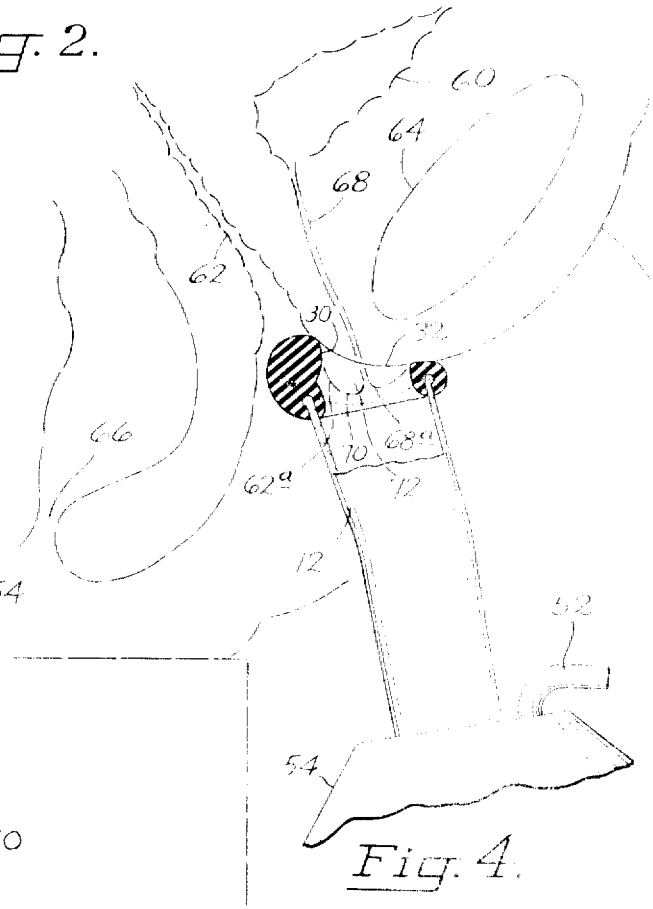
FIG. 4 illustrates in dashed outline a representative female pelvis in median section, and shows how the device is used to obtain urine samples.

Referring to FIG. 4, where a female pelvis is illustrated in median section with such female in a sitting position, bodily portions shown include a bladder 60, the vagina 62, the symphysis pubis 64, and rectum 66. The urethra which connects with the bladder is shown at 68 and the urethral meatus at 68a. The distal end of the anterior wall of the vagina is indicated at 62a, and it will be noted that the anterior wall of the vagina and tissue adjacent the urethral meatus form what is referred to herein as a vaginal vestibule angle designated at 70.

When using the device of the invention, as an initial step, the device is thoroughly sterilized so as to be free of contamination. The patient whose urine is to be analyzed may then be placed in a seated position with her legs spread slightly apart. To obtain a sample, the upper end of the tube with pad 14 thereon is inserted between the labia and the pad brought to bear on tissue surrounding the urethral meatus with the pad thus forming a sealed zone about the meatus. Positioning of the pad is accomplished by proper manipulation of the flask and lower portion of tube 12. In positioning the pad, shoulder 28 is utilized as a positioning aid by moving surface 30 of the shoulder against the distal end of the anterior vaginal wall. With the pad positioned so as to encircle the urethral meatus and vestibule angle, the pad is pressed firmly against the tissue surrounding the meatus so that through prolapse of the meatus and adjacent tissue a protrusion is formed (shown in FIG. 4 at 72) extending into the space bounded by the pad. The pad itself deforms somewhat, with shoulder 28 bending outwardly or to the left. In FIG. 4 it will be noted that surface 30 more nearly parallels the side wall of the tube than it does in FIG. 3. With outward bending of the shoulder, there is stretching and elongation of lips 32. Since the lips are bearing against tissue, they also tend to be compressed inwardly somewhat, and thus in FIG. 4 a concave curvature is illustrated for the edges of the lips which is not shown in FIG. 3.

Ultimately a snug fit is produced about tissue protrusion 72. Surface 30 forms a seal with the anterior wall of the vagina, and the pad lips and portion 34 likewise form a seal with the tissue around the meatus. Because of the angularity described in connection with plane C defined by the top of the pad, tube 12 extends out from the labia at the slight incline illustrated in FIG. 4, thus to clear any means used to support the patient in her seated position. With the bend described in the tube, proper drainage into the flask occurs.

It will be noted that there is no penetration of the urethra. A relatively small sealed region is produced by the pad which includes only a small portion of the anterior vaginal wall. Urine flowing into the flask in this manner is kept free from extraurethral contamination and this is done without incurring the danger of introducing bacteria into the urethra.

Upon completing the taking of a urine sample, it is an easy matter to remove the device from the patient, and afterwards separate the stopper from the flask to accommodate the removal of urine from the flask.

The device of the invention may be utilized as described in taking urine samples from female patients of widely different ages and physical descriptions. Results have indicated that reliable bacteria counts are obtainable using the method.

While there has been described an embodiment of the invention, variations and modifications are possible without departing therefrom. It is desired to cover all such modifications and variations as would be apparent to one skilled in the art, and that come within the scope of the appended claims.

It is claimed and desired to secure by Letters Patent:

1. A device for obtaining urine samples from the urethra, with such samples free of extraurethral contamination, comprising an elongated tube of stiff material having a passage extending therethrough wtih an entering end of the passage at one end of the tube, said tube between the ends thereof containing a bend whereby two reaches are present which define an obtuse angle, one of such reaches extending out to said one end of the tube, an annular pad of stretchable and more pliable material than the tube mounted on said one end of the tube and extending around said entering end of said passage, said pad including a shoulder on one side of the tube and said one end, which is disposed outwardly beyond said one end of the tube and bounded by an inner surface that slopes away from the axis of said tube progressing axially inwardly from said one end, said pad further including opposed lip means and a heel portion on the side of said tube opposite the tube's said one side which are outwardly beyond said one end of the tube and cooperate with said shoulder to bound said entering end and to produce encirclement of a urethral meatus and to form a seal thereabout with the device in operative position, said heel portion being disposed inwardly toward said one end of the tube from a plane passing through the outermost extremity of said shoulder and normal to the axis of said one end of the tube.

2. A device for obtaining urine samples from the urethra, with such samples free of extraurethral contamination, comprising an elongated tube having a passage extending therethrough with an entrance to said passage at one end of the tube, said tube being of stiff material to enable positioning of said one end by manipulation of the opposite end of the tube, an annular pad of compressible and resilient material mounted on said one end of the tube and extending around said entrance of said passage, said pad including a shoulder on one side of the tube disposed beyond said one end of the tube and supported by a flexible wall in said pad permitting said shoulder to deflect laterally of the tube, said pad further including oppositely disposed lip portions joining with opposite ends of said shoulder, which are disposed outwardly beyond said one end of the tube and are stretchable to permit elongation, and deflecting of said shoulder, said pad further including a heel portion disposed beyond said one end of the tube and on the side of the tube opposite the tube's said one side with opposite ends of the heel portion joining with said lip portions, said lip portions, heel portions, and shoulder cooperating to produce encirclement of a urethral meatus and to form a seal thereabout with the device in operative position, said heel portion being disposed inwardly toward said one end of the tube from a plane passing through the outermost extremity of said shoulder and normal to the axis of said one end of the tube.

*3. The device of claim 2 wherein said lip portions, heel portions, and shoulder are adapted by their shape and position to produce close encirclement of the urethral meatus to form a seal immediately thereabout with the device in operative position.*

*4. A device for obtaining urine from the urethra, said device comprising: an elongated relatively stiff tube portion having a passageway extending therethrough with an entrance to said passageway at one end of the tube portion, said tube portion being of such stiffness as to enable insertion and positioning of said one end of the tube portion within the female user by manipulation of the opposite end of the tube portion; and an annular pad-like portion of resilient material on said one end of the tube portion and having an open-ended urine passage forming a continuation of said entrance of said tube portion passageway, said pad-like portion including an intermost shoulder adapted by its shape and position to engage the anterior wall of the vagina, said shoulder being part of a flexible wall in said pad-like portion which permits said shoulder to deflect laterally of the tube, said pad-like portion further including oppositely disposed lip sections joining with opposite ends of said shoulder and defining with said shoulder part of a urine entryway to said open-ended urine passage, said lip sections being stretchable to permit deflection thereof and of said shoulder, said pad-like portion further including a heel section joining with the end of said lip sections opposite that connected to said shoulder, said heel section being disposed inwardly toward said one end of the tube portion relative to a transverse plane passing through the outermost extremity of said shoulder and normal to the longitudinal axis of said one end of the tube portion.*

*5. The device of claim 4 wherein said heel section of said pad-like portion is adapted by its shape and position to engage the interior female surfaces immediately anterior to the urethral meatus, so the seal formed about the urethral meatus is immediately around the same, wherein urine samples may be obtained substantially free of extra-urethral contamination.*

References Cited

The following references, cited by the Examiner, are of record in the patented file of this patent or the original patent.

UNITED STATES PATENTS

| | | | |
|---|---|---|---|
| 70,087 | 10/1867 | Hadfield | 128—300 |
| 268,555 | 12/1882 | Simpson | 4—110 |
| 1,510,973 | 10/1924 | Behan | 4—110 |
| 2,382,276 | 8/1945 | Wells | 4—110 |
| 2,490,969 | 12/1949 | Kinyon | 128—295 |
| 3,122,139 | 2/1964 | Jones | 128—275 |
| 3,259,920 | 7/1966 | Voller | 4—110 |

RICHARD A. GAUDET, Primary Examiner

K. L. HOWELL, Assistant Examiner

U.S. Cl. X.R.

4—110; 128—295